US005195508A

United States Patent [19]

Müller et al.

[11] Patent Number: 5,195,508

[45] Date of Patent: Mar. 23, 1993

[54] SPARK GAP UNIT FOR LITHOTRIPSY

[75] Inventors: Michael Müller, Schondorf; Peter Buchbauer, Garching; Harald Eizenhöfer, Munich; Friedrich Ueberle, Gilching; Herbert Weiler, Alling; Reiner Schultheiss, Eching, all of Fed. Rep. of Germany

[73] Assignee: Dornier Medizintechnik GmbH, Fed. Rep. of Germany

[21] Appl. No.: 701,817

[22] Filed: May 17, 1991

[30] Foreign Application Priority Data

May 18, 1990 [DE] Fed. Rep. of Germany ....... 4016054

[51] Int. Cl.$^5$ ........................................ A61B 17/22

[52] U.S. Cl. ........................ 128/24 EL; 606/128; 367/147; 313/141

[58] Field of Search ........................ 606/127, 128; 128/24 EL; 367/142, 147; 313/130, 118, 141, 142; 123/169 EL, 160 E, 169 P

[56] References Cited

U.S. PATENT DOCUMENTS

| | | | |
|---|---|---|---|
| 4,580,894 | 4/1986 | Wojcik . | |
| 4,608,983 | 9/1986 | Müller et al. | 128/24 EL |
| 4,809,682 | 3/1989 | Forssmann et al. | 128/24 EL |
| 4,938,781 | 7/1990 | Pimiskern | 128/24 EL |
| 4,940,050 | 7/1990 | Forssmann et al. | 128/24 EL |

FOREIGN PATENT DOCUMENTS

| | | | |
|---|---|---|---|
| 0196353 | 10/1986 | European Pat. Off. | 128/24 EL |
| 0257199 | 3/1988 | European Pat. Off. . | |
| 0338618 | 10/1989 | European Pat. Off. . | |
| 0377901 | 7/1990 | European Pat. Off. . | |
| 2635635 | 5/1979 | Fed. Rep. of Germany . | |
| 3150430 | 12/1981 | Fed. Rep. of Germany . | |
| 3316837 | 5/1983 | Fed. Rep. of Germany . | |
| 3543881 | 12/1985 | Fed. Rep. of Germany . | |
| 3517934 | 11/1986 | Fed. Rep. of Germany . | |
| 3622352 | 12/1987 | Fed. Rep. of Germany | 128/24 EL |
| 3814468 | 11/1988 | Fed. Rep. of Germany | 128/24 EL |
| 3739230 | 6/1989 | Fed. Rep. of Germany . | |
| 1227185 | 4/1986 | U.S.S.R. | 128/24 EL |

*Primary Examiner*—Lee S. Cohen
*Assistant Examiner*—Krista Pfaffle
*Attorney, Agent, or Firm*—Evenson, Wands, Edwards, Lenahan & McKeown

[57] ABSTRACT

A spark gap unit that is easy to manufacture and significantly lighter than previously used spark gap units for generating underwater shock waves, particularly for non-invasive lithotripsy, has an internal conductor with an inner electrode, an insulation which at least partially envelops the internal conductor, and an external conductor with a bow and an outer electrode. The internal conductor is significantly shorter than the external conductor, and the external conductor at the rearward end of the spark gap unit projects beyond the internal conductor. The internal conductor, the insulation, and the external conductor are coaxially arranged. An outside diameter of the internal conductor is relatively small in comparison to an inside diameter of the external conductor. The spark gap unit has a hollow space inside the insulation, this hollow space being open in the direction of a rearward end of the spark gap unit. In the opposite direction from the rearward end, the hollow space is bounded by the internal conductor itself and the envelopment of the internal conductor by the insulation.

10 Claims, 2 Drawing Sheets

FIG. 1
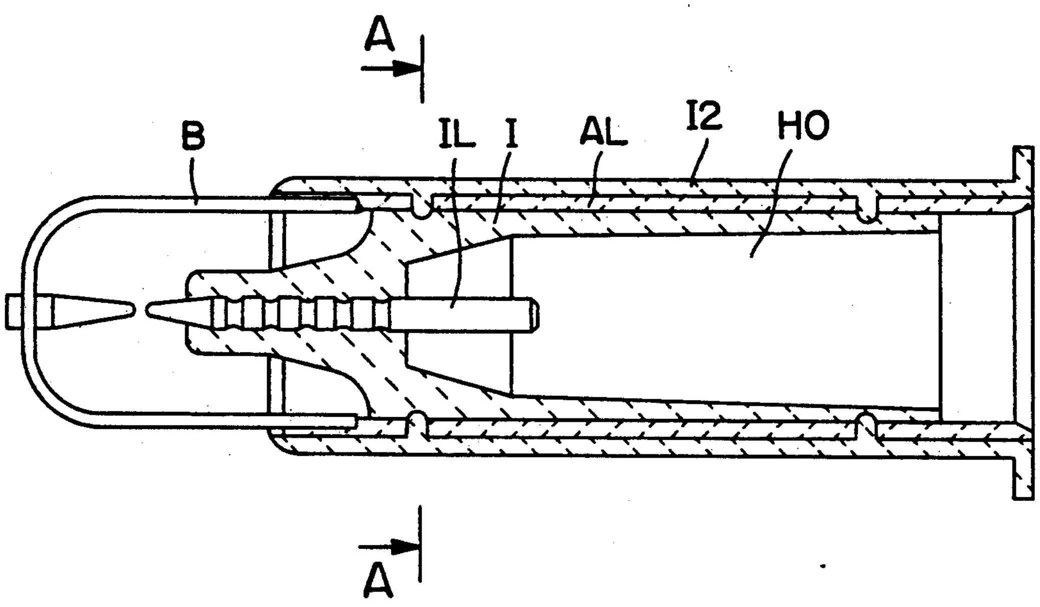
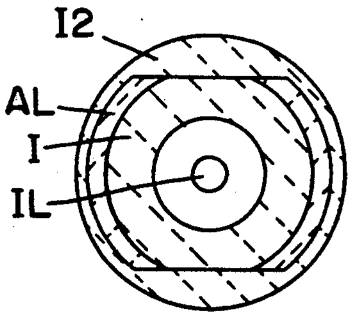
FIG. 3

SPARK GAP UNIT FOR LITHOTRIPSY

BACKGROUND AND SUMMARY OF THE INVENTION

The present invention relates to a spark gap unit for generating underwater shock waves, particularly for non-invasive lithotripsy, having a coaxial arrangement of an internal conductor with an inner electrode, an insulation, and an external conductor with a bow and an outer electrode.

This type of a spark gap unit is known from the German Patent Document DE-PS 26 35 635. A spark gap unit with an optimized distribution of the lines of electric flux is described in German Patent Document DE-PS 35 43 881.

An object of the present invention is to provide an improved spark gap unit for the generating of shock waves and which can be manufactured at lower cost.

This and other objects are achieved by the present invention which provides a spark gap unit for generating underwater shock waves, particularly for non-invasive lithotripsy, has an internal conductor with an inner electrode, an insulation which at least partially envelops the internal conductor, and an external conductor with a bow and an outer electrode. The internal conductor is significantly shorter than the external conductor, and the external conductor at the rearward end of the spark gap unit projects beyond the internal conductor. The internal conductor, the insulation, and the external conductor are coaxially arranged. An outside diameter of the internal conductor is relatively small in comparison to an inside diameter of the external conductor. The spark gap unit has a hollow space inside the insulation, this hollow space being open in the direction of a rearward end of the spark gap unit. In the opposite direction from the rearward end, the hollow space is bounded by the internal conductor itself and the envelopment of the internal conductor by the insulation so that a "hat-shape type" insulation is obtained.

As a result of the interior internal conductor contacting, material is saved which results in lower manufacturing costs and, because of the lower weight, also in lower transport costs. An embodiment of the spark gap unit according to the invention, as a result of a thicker bow to the external conductor point, has a higher mechanical stability, resulting in a longer service life. In another embodiment, a twisting of the bow arms about the longitudinal axis of the spark gap unit may be provided so that an elastic effect occurs. The arms of the bow will then not extend in parallel to the longitudinal axis of the spark cap unit but, together with it, enclose an angle $\neq 0°$ which causes them to have the effect of a torsion spring. In all embodiments, the bow material may be selected to be equal or similar to the point material. The insulation is preferably manufactured of injection-molded plastic and mechanically holds the internal conductor point, and provides an electrical insulation between the internal and external conductor.

By these provisions, the internal conductor may have relatively small dimensions. It may be implemented, for example, by a relatively narrow metal pin. Its mechanical stability is now provided by the insulation, in contrast to previous spark gap units whose shaping essentially followed the internal conductor. This saving of metal reduces the overall weight of the spark gap unit.

The ratio of the inside diameter of the external conductor to the outside diameter of the internal conductor is preferably in the range of from 3:1 to 8:1. The length of the internal conductor preferably amounts to 20-60% of the length of the external conductor.

In an embodiment of the present invention, the slope of the lines of electrical flux is optimized which results in a more uniform ignition (less scattering) and a longer service life. This is achieved by appropriate shaping of the boundary surface between the insulator point and the water in the point area of the internal conductor, corresponding to the characteristics already known from German Patent Document DE-PS 35 43 881, particularly the stronger construction of the insulator point. As a result an electrical flux line focussing (constriction) on the axis is achieved which leads to a more uniform spark jump.

In an advantageous embodiment of the present invention, a bow is used having an even number of arms, in particular, having only two arms for the holding of the outer electrode. The result is a lower shading of the shock wave than in models with more arms, higher efficiency, and a longer service life, if the arms are dimensioned correspondingly. In an embodiment of the invention, the arms consist of a material of a thickness of 2 mm, such as steel.

In another embodiment, the spark gap unit is surrounded by a second insulation which has projections that engage in notches of the external conductor and reach to the inner insulation. As a result, the spark gap unit is provided with high mechanical stability.

Other objects, advantages and novel features of the present invention will become apparent from the following detailed description of the invention when considered in conjunction with the accompanying drawings.

BRIEF DESCRIPTION OF THE DRAWINGS

FIG. 1 shows a longitudinal cross-sectional view of a spark gap constructed in accordance with an embodiment of the present invention.

FIG. 3 shows a cross-sectional view of the embodiment of FIG. 1 along the line A—A.

DETAILED DESCRIPTION OF THE DRAWINGS

Figure 2:
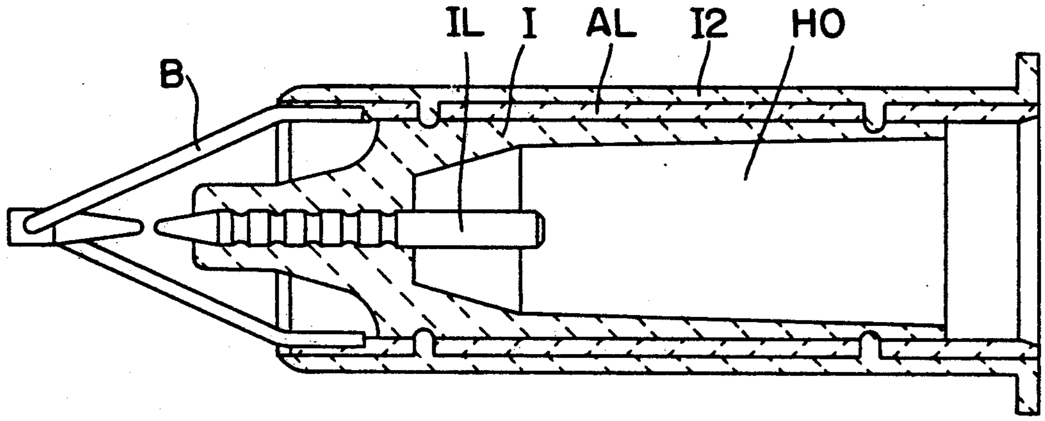
FIG. 2 shows a longitudinal cross-sectional view of a spark gap with another embodiment of the present invention.

FIGS. 1 and 2 each show an embodiment of a spark gap unit according to the present invention. The internal conductor IL is separated from the external conductor AL by the insulation I. The coaxial construction of the two conductors IL and AL is clearly visible. In the illustrated embodiment, the external conductor AL is surrounded by a second insulation I2. The two arms of the bow B, which carry the external conductor electrode, are fastened to the external conductor AL on its left-hand side (in FIGS. 1 and 2). Also, on the left-hand side, the internal conductor IL tapers toward the inner electrode which is opposite the outer electrode. The internal conductor IL has an extensive stamping (ribbing) by means of which it is anchored in the injection-molded part of the insulation I.

It is clearly recognizable that the outside diameter of the internal conductor IL is relatively small in comparison to the inside diameter of the external conductor. The external conductor AL is much longer than the internal conductor IL and, at the rearward end of the spark gap unit, projects far beyond the internal conductor.

Inside the insulation I, the spark gap unit has a hollow space HO which is open in the direction of the rearward end of the spark gap and which, in the opposite direction, is bounded by the internal conductor IL itself and its envelopment by the insulation I. Measured along the main axis of the spark gap unit, the hollow space HO has a length of several centimeters in this embodiment.

The insulation I carries the internal conductor IL and protects it from displacements. The hollow space HO in the insulation I extends in the manner of a cylinder or, as shown in FIG. 1 and 2, slightly conically, and may therefore be used for an easy placement on the current-feeding plug. On the rearward end, the external conductor insulation 12 is reinforced in a ring-shaped manner so that the spark gap unit can easily be pulled out of the apparatus on this ring.

FIG. 3 is a sectional view along Line A—A in FIG. 1 of a spark gap unit according to the invention. The coaxial construction with the internal conductor IL, the surrounding insulation I, the external conductor AL and the second insulation I2 is clearly visible in this figure. The section A—A is placed on a point on which the external conductor AL has breakthroughs through which the outer insulation I2 can reach through to the inner insulation I, resulting in a type of snap closure for a secure interconnection and a simple manufacturing of the whole spark gap unit.

FIG. 2 illustrates an embodiment of a spark gap unit according to the invention having twisted bow arms B which therefore demonstrate a stronger spring effect. Along their whole length, which projects out of the insulator, the arms B, in this case, do not extend in parallel to the main axis of the spark gap unit but are twisted against it (axis of rotation is identical with the main axis of the spark gap unit). An embodiment is also possible, but not shown, in which the bow arms project out of the insulator in parallel to the main axis of the spark gap unit, after a bend extend somewhat diagonally with respect to the main axis, and after another bend, again extend in parallel to the main axis up to the front.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. A spark gap unit for generating underwater shock waves, particularly for non-invasive lithotripsy, comprising:
   - an internal conductor with an inner electrode;
   - an insulation which at least partially envelops the internal conductor;
   - an external conductor with a bow and an outer electrode, the internal conductor being significantly shorter than the external conductor, and the external conductor at a rearward end of the spark gap unit projecting beyond the internal conductor;
   - said internal conductor, said insulation, and said external conductor being coaxially arranged, and an outside diameter of the internal conductor being relatively small in comparison to an inside diameter of the external conductor, and wherein
   - the spark gap unit has a hollow space inside the insulation, said hollow space being open in the direction of a rearward end of the spark gap unit and which, in the opposite direction from the rearward end, is bounded by the internal conductor itself and the envelopment of the internal conductor by the insulation.

2. A spark gap unit according to claim 1, wherein the bow has an even number of arms.

3. A spark gap unit according to claim 2, wherein the number of arms is two.

4. A spark gap unit according to claim 2, further comprising a second insulation that surrounds external conductor.

5. A spark gap unit according to claim 4, wherein the second insulation is enlarged in a ring-shaped manner toward the rearward end of the spark gap unit.

6. A spark gap unit according to claim 5, wherein the arms of the bow are twisted such that the arms extend at least partially at a non-zero angle with respect to a longitudinal axis of the spark gap unit.

7. A spark gap unit according to claim 1, further comprising a second insulation that surrounds the external conductor.

8. A spark gap unit according to claim 7, wherein the second insulation is enlarged in a ring-shaped manner toward the rearward end of the spark gap unit.

9. A spark gap unit according to claim 8, wherein the arms of the bow are twisted such that the arms extend at least partially at a non-zero angle with respect to a longitudinal axis of the spark gap unit.

10. A spark gap unit according to claim 1, wherein the arms of the bow are twisted such that the arms extend at least partially at a non-zero angle with respect to a longitudinal axis of the spark gap unit.

* * * * *